US010646200B2

(12) United States Patent
Kantor et al.

(10) Patent No.: US 10,646,200 B2
(45) Date of Patent: May 12, 2020

(54) INTRAVASCULAR ULTRASOUND IMAGING SYSTEM WITH SLIP RING INTERFACE AND ASSOCIATED DEVICES, SYSTEMS, AND METHODS

(71) Applicant: Volcano Corporation, San Diego, CA (US)

(72) Inventors: Sherwood Kantor, Sacramento, CA (US); Douglas E. Meyer, Folsom, CA (US); Duane De Jong, Elk Grove, CA (US); Paul Hoseit, El Dorado Hills, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 405 days.

(21) Appl. No.: 14/845,093

(22) Filed: Sep. 3, 2015

(65) Prior Publication Data

US 2016/0066886 A1   Mar. 10, 2016

Related U.S. Application Data

(60) Provisional application No. 62/046,002, filed on Sep. 4, 2014.

(51) Int. Cl.
*A61B 8/12* (2006.01)
*A61B 8/00* (2006.01)
*A61B 8/08* (2006.01)

(52) U.S. Cl.
CPC .......... *A61B 8/4461* (2013.01); *A61B 8/0891* (2013.01); *A61B 8/12* (2013.01); *A61B 8/445* (2013.01); *A61B 8/4411* (2013.01)

(58) Field of Classification Search
CPC ......... A61B 8/445; A61B 8/0891; A61B 8/12; A61B 8/4411; A61B 8/4461
See application file for complete search history.

(56) References Cited

U.S. PATENT DOCUMENTS

| 5,115,814 A * | 5/1992 | Griffith | ............... A61B 5/06 600/439 |
| 6,641,540 B2 | 11/2003 | Fleischman et al. | |

(Continued)

FOREIGN PATENT DOCUMENTS

| JP | 2006174883 A | 7/2006 |
| JP | 2013048802 A | 3/2013 |

(Continued)

*Primary Examiner* — Mark D Remaly

(57) ABSTRACT

An intravascular ultrasound (IVUS) imaging system is provided. The IVUS imaging system includes an intravascular device including a transducer shaft with an ultrasound transducer at a distal end. The IVUS imaging system also includes an interface module removably coupled to the intravascular device. The interface module includes a connector rotatably coupled to a proximal end of the transducer shaft; a motor coupled to the connector; a spinning element coupled to the motor, wherein the spinning element comprises four conductive rings; a stationary element comprising a plurality of brushes, wherein the stationary element is disposed proximate the spinning element such that a different one of the plurality of brushes is in mechanical contact with each of the four conductive rings; and four conductors coupled to the connector and the spinning element such that the stationary element and the intravascular device are in electrical communication.

22 Claims, 4 Drawing Sheets

(56) References Cited

U.S. PATENT DOCUMENTS

| | | | |
|---|---|---|---|
| 8,864,674 B2 | 10/2014 | Corl | |
| 2010/0249601 A1 | 9/2010 | Courtney | |
| 2013/0218020 A1* | 8/2013 | Corl | A61B 8/12 600/467 |
| 2013/0303919 A1* | 11/2013 | Corl | A61B 8/4494 600/467 |
| 2014/0107488 A1 | 4/2014 | Fearnot | |
| 2014/0142432 A1 | 5/2014 | Hutchins | |
| 2015/0305708 A1* | 10/2015 | Stigall | A61B 5/02007 600/467 |

FOREIGN PATENT DOCUMENTS

| | | | |
|---|---|---|---|
| WO | 2008057573 | A2 | 5/2008 |
| WO | 2010104775 | A2 | 9/2010 |

\* cited by examiner

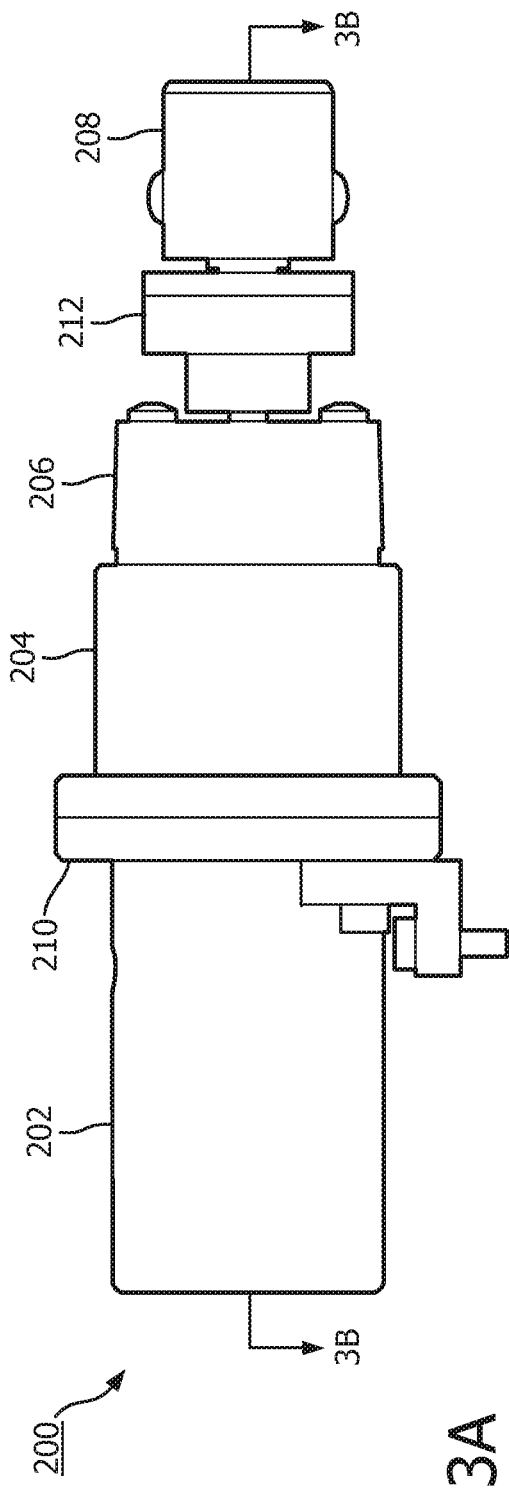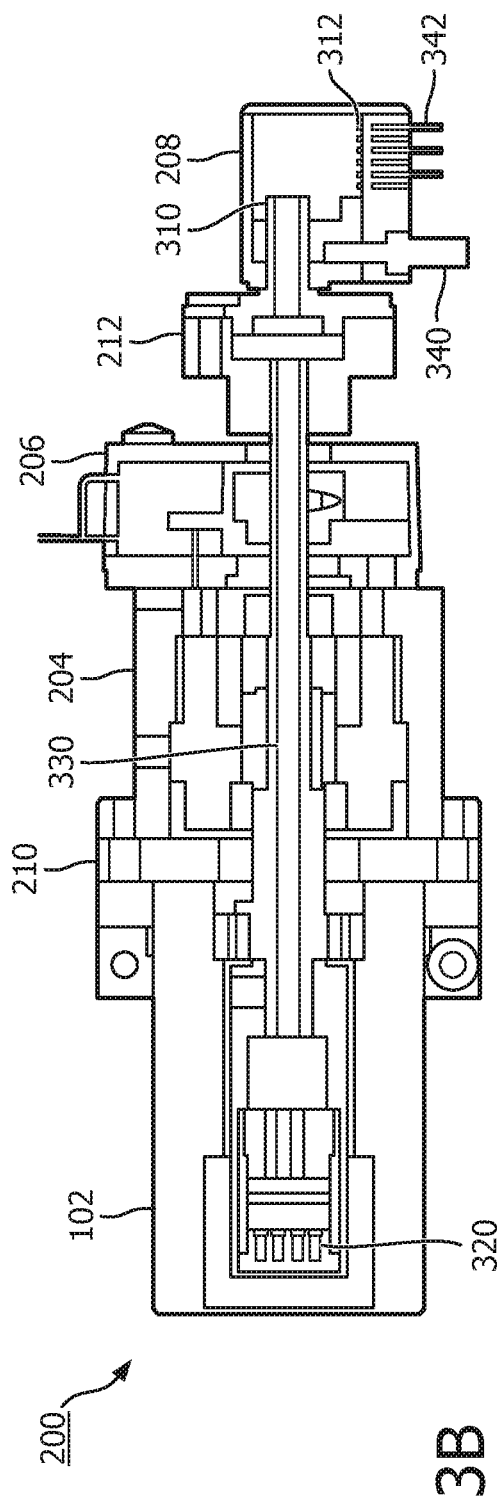
FIG. 3A
FIG. 3B

INTRAVASCULAR ULTRASOUND IMAGING SYSTEM WITH SLIP RING INTERFACE AND ASSOCIATED DEVICES, SYSTEMS, AND METHODS

CROSS REFERENCE TO RELATED APPLICATIONS

The present application claims priority to and the benefit of the U.S. Provisional Patent Application No. 62/046,002, filed Sep. 4, 2014, which is hereby incorporated by reference in its entirety.

TECHNICAL FIELD

The present disclosure relates generally to an interface module of a rotational intravascular ultrasound (IVUS) imaging system with a slip ring interface that facilitates the transfer of both alternating current (AC) and direct current (DC) signals between rotating and stationary portions.

BACKGROUND

Minimally invasive sensing systems are routinely utilized by medical professionals to evaluate, measure, and diagnose conditions within the human body. As one example, intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device includes one or more ultrasound transducers arranged at a distal end of an elongate member. The elongate member is passed into the vessel thereby guiding the transducers to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

There are two general types of IVUS devices in use today: rotational and solid-state (also known as synthetic aperture phased array). For a typical rotational IVUS device, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS devices utilize a scanner assembly that includes an array of ultrasound transducers distributed around the circumference of the device connected to a set of transducer controllers. The transducer controllers select transducer sets for transmitting an ultrasound pulse and for receiving the echo signal. By stepping through a sequence of transmit-receive sets, the solid-state IVUS system can synthesize the effect of a mechanically scanned transducer element but without moving parts. Since there is no rotating mechanical element, the transducer array can be placed in direct contact with the blood and vessel tissue with minimal risk of vessel trauma. Furthermore, because there is no rotating element, the interface is simplified. The solid-state scanner can be wired directly to the imaging system with a simple electrical cable.

Conventional rotational IVUS catheters are interfaced to the non-rotating or stationary part of the IVUS imaging system by means of a rotary transformer. The rotary transformer is comprised of two sections: a rotating section that is mounted on the shaft of a motor that rotates the catheter driveshaft and a non-rotating section that is mounted in close proximity to the rotating section. The two sections are separated by an air gap. AC signals are transmitted across this rotating interface by means of transformer action. Rotational IVUS catheters that have a piezoelectric zirconate transducer (PZT) can be implemented with transmission of only AC signals (e.g., excitation signals to the PZT element and/or return signals from the PZT element to the IVUS console). However, catheters with advanced transducer technologies, such as piezoelectric micromachined ultrasonic transducers (PMUT), include electronic components that require DC power. Since a rotary transformer couples only time varying signals, it cannot be used to transmit a DC signal or voltage to the rotating side of the imaging system.

Thus, while existing rotary interfaces have proved useful, there remains a need for improvements in the design to allow advanced transducer technologies to be implemented. Accordingly, the need exists for improvements to the interface module of the rotational IVUS imaging system.

SUMMARY

Embodiments of the present disclosure provide a slip ring assembly within an interface module of a rotational intravascular ultrasound (IVUS) imaging system. The IVUS imaging system includes an intravascular device, such as an IVUS catheter, with an ultrasound transducer and/or other electronic components. The slip ring assembly allows alternating current (AC) and direct current (DC) signals to be transmitted from a stationary portion of the IVUS imaging system to a rotary portion. Thus, in some embodiments, DC power is transmitted to an amplifier for a piezoelectric micromachined ultrasonic transducer (PMUT) in the intravascular device.

In an exemplary aspect, the present disclosure is directed to an intravascular ultrasound (IVUS) imaging system. The IVUS imaging system includes an intravascular device including a transducer shaft with an ultrasound transducer at a distal end; and an interface module removably coupled to the intravascular device, the interface module including: a connector rotatably coupled to a proximal end of the transducer shaft; a motor coupled to the connector; a spinning element coupled to the motor, wherein the spinning element comprises four conductive rings; a stationary element comprising a plurality of brushes, wherein the stationary element is disposed proximate the spinning element such that a different one of the plurality of brushes is in mechanical contact with each of the four conductive rings; and four conductors coupled to the connector and the spinning element such that the stationary element and the intravascular device are in electrical communication.

In some aspects, the intravascular device further comprises an electronic component in electrical communication with the stationary element of the interface module. In some aspects, the ultrasound transducer comprises a piezoelectric micromachined ultrasonic transducer (PMUT). In some aspects, the electronic component comprises an amplifier. In some aspects, the spinning element is disposed between the connector and the motor. In some aspects, the motor is disposed between the connector and the spinning element. In some aspects, the interface module further comprises a hollow shaft extending through the motor, and between the connector and the spinning element. In some aspects, the four conductors are at least partially disposed within the hollow shaft. In some aspects, the hollow shaft is electrically grounded. In some aspects, the interface module comprises at least five conductors. In some aspects, the intravascular device further comprises four conductors coupled to the ultrasound transducer and a connector hub at the proximal end of the transducer shaft, wherein, when the connector hub of the intravascular device is connected to the connector of interface module, the stationary portion of the interface module is in electrical communication with the ultrasound transducer. In some aspects, the interface module further comprises an encoder.

In another exemplary aspect, the present disclosure is directed to an interface module for an intravascular ultrasound imaging system. The interface module includes a connector rotatably coupled to a transducer shaft of an intravascular device; a motor coupled to the connector; a spinning element coupled to the motor, wherein the spinning element comprises four conductive rings; a stationary element comprising a plurality of brushes, wherein the stationary element is disposed proximate the spinning element such that a different one of the plurality of brushes is in mechanical contact with each of the four conductive rings; and four conductors coupled to the connector and the spinning element such that the stationary element and the intravascular device are in electrical communication.

In some aspects, the motor is disposed between the connector and the spinning element. In some aspects, the interface module further comprises a hollow shaft extending through the motor, and between the connector and the spinning element, wherein the four conductors are at least partially disposed within the hollow shaft. In some aspects, the hollow shaft is electrically grounded.

In another exemplary aspect, the present disclosure is directed to an interface module for an intravascular ultrasound device. The interface module includes a connector rotatably coupled to a transducer shaft of the intravascular ultrasound device; a motor coupled to the connector such that the connector rotates when the motor is activated, wherein the motor comprises a hollow shaft extending therethrough; a slip ring assembly coupled to the motor, wherein the slip ring assembly includes a plurality of conductive rings and a plurality of brushes, wherein each of the plurality of brushes are in mechanical contact with at least one of the plurality of conductive rings, and wherein the slip ring assembly is coupled to the motor such that the plurality of conductive rings rotates when the motor is activated; and a plurality of conductors at least partially disposed within the hollow shaft, wherein the plurality of conductors electrically couple the connector and the plurality of conductive rings.

In some aspects, the plurality of conductors comprises at least four conductors. In some aspects, the hollow shaft is electrically grounded. In some aspects, the slip ring assembly is disposed between the connector and the motor. In some aspects, the motor is disposed between the connector and the slip ring assembly. In some aspects, the interface module further comprises an encoder.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 3a is a diagrammatic side view of an interface module according to aspects of the present disclosure.

FIG. 3b is a diagrammatic, cross-sectional, top view of the interface module of FIG. 3a.

FIG. 4b is a diagrammatic, cross-sectional, top view of the interface module of FIG. 4a.

DETAILED DESCRIPTION

Figure 1:
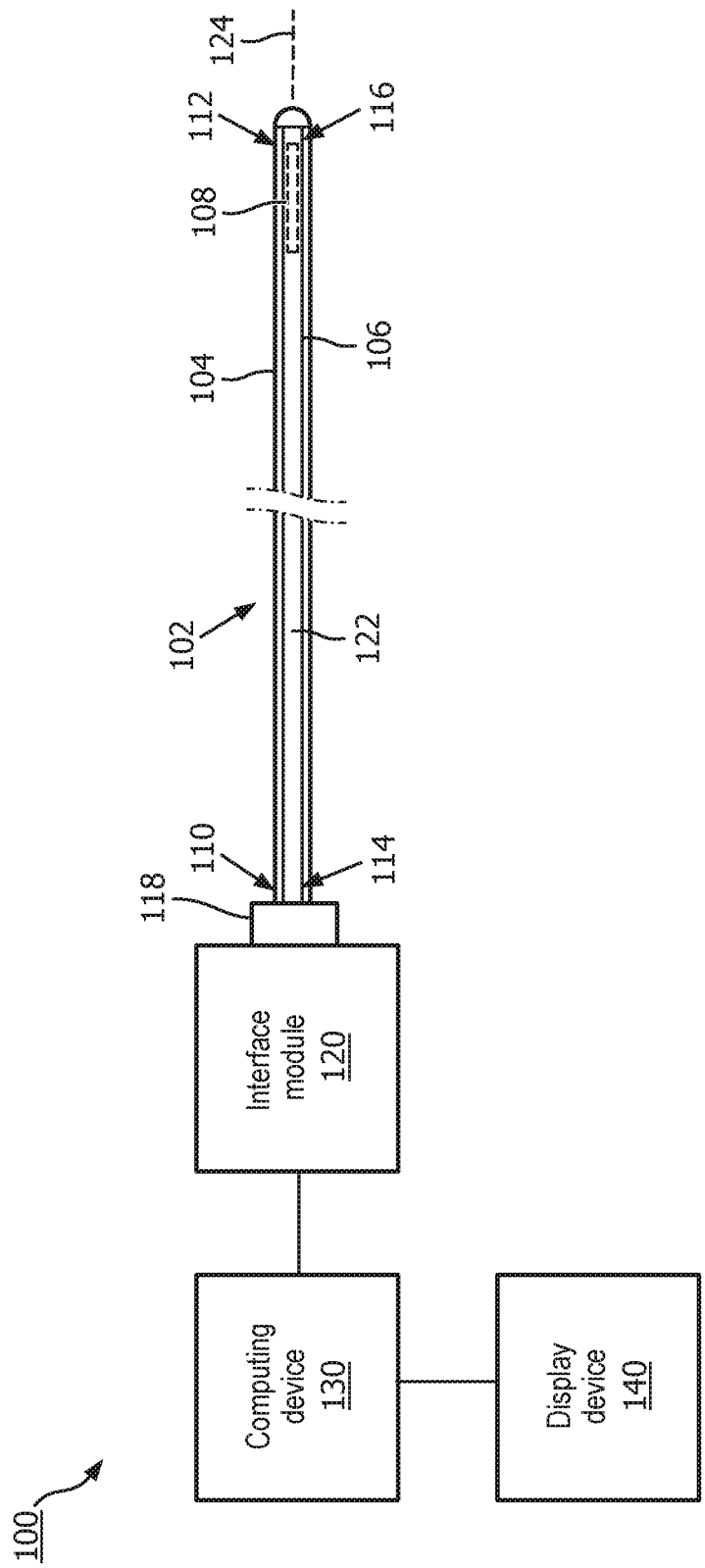
FIG. 1 is a diagrammatic schematic view of an intravascular ultrasound (IVUS) imaging system according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the minimally invasive medical sensing system is illustrated an IVUS system configured for cardiovascular imaging, it is understood that the sensing system is not intended to be limited to this application. The techniques and structures disclosed herein are equally adaptable for use in other medical sensing systems. Further, the IVUS system disclosed herein equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Embodiments of the present disclosure provide devices, systems, and methods for an interface module including a slip ring assembly in a rotational IVUS imaging system. The slip ring assembly facilitates the transfer of time varying or AC signals as well as DC signals. The slip ring assembly includes rotating conductive rings in mechanical contact with stationary brushes, providing direct electrical connection across the rotating interface. As a result, both AC and DC signals can be passed from the stationary to the rotating side. An interface module capable of transferring both AC and DC signals between rotating and stationary portions of the IVUS imaging system allows the use of advanced transducer components, such as a PMUT element. For example, a transducer assembly with a PMUT can also include an amplifier that receives and amplifies signals representative of ultrasound echoes received by the PMUT element. DC power can be provided to the amplifier from the stationary portion of the imaging system to the rotating portion via the slip ring assembly. AC signals, such as radiofrequency signals representative of ultrasound returns, can also be transmitted across the slip ring assembly.

In some embodiments, the interface module includes a connector that is removably coupled to an intravascular device having an ultrasound transducer. The ultrasound transducer is also electrically connected to the interface module via the connector. The interface module includes a motor that is coupled to the connector and that rotates a drive cable of the intravascular device when the motor is activated. The motor is also coupled to the slip ring assembly and rotates the conductive rings when the motor is activated. Conductors extend from the connector to the conductive rings to electrically connect the connector and the slip ring assembly. As a result, the intravascular device (e.g., the transducer element and/or other electronic components) are electrically connected to the stationary brushes of the slip ring assembly. This is because the intravascular device is electrically coupled to the connector, the conductors electrically couple the connector and the conductive rings, and the conductive rings are electrically coupled to the stationary brushes. Thus, AC and DC signals can be transmitted from the stationary brushes to the transducer element and/or other electronic components of the intravascular device (and/or vice versa, from the rotating portion of the imaging system to the stationary portion). In some embodiments, the conductors of the interface module are disposed within a hollow shaft that extends through the motor. In some embodiments, four conductors electrically couple a connector of the interface module and the spinning element of the slip ring assembly.

FIG. 1 is a diagrammatic schematic view of an intravascular ultrasound (IVUS) imaging system 100 according to an embodiment of the present disclosure. At a high level, the IVUS imaging system 100 includes an intravascular device 102 coupled by an interface module 120 (also referred to as a patient interface module or PIM) to a computing device 130. The computing device 130 is coupled to a display device 140 that displays IVUS images, such the IVUS images generated by the IVUS imaging system 100 based on the data obtained by the intravascular device 102.

The intravascular device 102 (such as a catheter, guide wire, or guide catheter) is capable of collecting ultrasound data while positioned within a vessel (such as a blood vessel). The intravascular device 102 has an elongate body 104 and an elongate transducer shaft 106. The body 104 is flexible and has both a proximal portion 110 and a distal portion 112. The body 104 can be a sheath surrounding the flexible transducer shaft 106. For explanatory purposes, the body 104 in FIG. 1 is illustrated as visually transparent such that the transducer shaft 106 disposed therein can be seen, although it will be appreciated that the body 104 may or may not be visually transparent. The transducer shaft 106 can be flushed with a sterile fluid, such as saline, within the body 104. The fluid serves to eliminate air pockets around the transducer shaft 106 that adversely affect quality of the IVUS images generated by the intravascular device 102. The fluid can also act as a lubricant. The transducer shaft 106 has a proximal end portion 114 disposed within the proximal end portion 110 of the body 104 and a distal end portion 116 disposed within the distal end portion 112 of the body 102.

The distal portion 112 of the body 102 and the distal portion 116 of the transducer shaft 106 are inserted into a patient during the operation of the intravascular device 102. In that regard, the IVUS imaging system 100 may be utilized in a variety of applications and can be used to image vessels and structures within a living body. For example, the vessels can be fluid filled or surrounded structures, both natural and man-made, within a living body and can include for example, but without limitation, structures such as: organs including the liver, heart, kidneys, gall bladder, pancreas, lungs; ducts; intestines; nervous system structures including the brain, dural sac, spinal cord and peripheral nerves; the urinary tract; as well as valves within the blood or other systems of the body. In addition to imaging natural structures, the images may also include imaging man-made structures such as, but without limitation, heart valves, stents, shunts, filters and other devices positioned within the body. The usable length of the intravascular device 102 (e.g., the portion that can be inserted into a patient) can be any suitable length and can be varied depending upon the application.

The transducer shaft 106 includes a drive cable 122 and a transducer subassembly 108 at the distal portion 116. The transducer subassembly 108 can be coupled to and/or disposed within a transducer housing. The transducer subassembly 108 and/or the transducer housing is attached to the drive cable 122 at the distal end portion 116 of the transducer shaft 104. The drive cable 122 is rotated within the body 102 about a longitudinal axis 124 by a motor within the interface module 120, as described within respect to FIGS. 2-4b. Rotation of the drive cable 122 in turn causes rotation of transducer subassembly 108 and/or the transducer housing about the longitudinal axis 124.

The transducer assembly 108 can include a single transducer element that is disposed at the distal portion 116 of the transducer shaft 106. The transducer subassembly 108 can include any suitable type of ultrasound transducer. In an embodiment, the transducer element is a piezoelectric micromachined ultrasound transducers (PMUT) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer is a piezoelectric zirconate transducer (PZT) transducer, such as bulk PZT transducer, capacitive micromachined ultrasound transducer (CMUT), single crystal piezoelectric material, other suitable ultrasound transmitter and receiver, and/or combination thereof. The transducer subassembly 108 can additionally include one or more electronic components electrically connected to and/or otherwise in communication with the transducer element. For example, the transducer subassembly 108 can include control circuitry for controlling emission of ultrasonic energy from the transducer element and acquisition of return echoes. For example, the transducer subassembly 108 can include an application specific integrated circuit (ASIC), an amplifier, a pulser, a protect circuit, timing and control circuitry, and/or other suitable components. The amplifier can receive and amplify signals representative of ultrasound echoes received by the transducer element, as may be needed in some circumstances when the transducer element is a PMUT. An intravascular device utilizing a PMUT element is described in Paul Douglas Corl, U.S. patent application Ser. No. 13/892,045, "Circuit Architectures and Electrical Interfaces for Rotational Intravascular Ultrasound (IVUS) Devices," filed May 10, 2013, now U.S. Pat. No. 8,864,674 issued Oct. 21, 2014, the entirety of which is hereby incorporated by reference herein. As described herein, DC power can be provided to the amplifier between stationary and rotating portions of the imaging system 100 via the slip ring assembly of the interface module.

The intravascular device 102 is coupled to the interface module 120. In that regard, the proximal end portion 110 of the body 104 and the proximal end portion 114 of the transducer shaft 106 are mechanically connected to the interface module 120. For example, the proximal end portions 110, 114 are fitted with a catheter hub 118 that is removably connected to the interface module 120. Connection of the intravascular device 102 and the interface module 120 via the catheter hub 118 facilitates mechanical and electrical connection between components of the intravascular device 102 and the interface module 120. For example, the transducer shaft 106 can be rotatably coupled to a catheter connector within the interface module 120 such that the motor within the interface module 120 rotates the drive cable 122 and the transducer subassembly 108. The catheter hub 118 can include a mating component with electrical contacts that facilitates the transfer of electric signals between the intravascular device 102 and the interface module 120. Additionally, the interface module 120 provides a transition between a rotating portion of the IVUS imaging system 100 and a stationary portion. As described herein, slip ring(s) can be implemented in the interface module 120 to facilitate the transfer of both AC and DC signals across the rotary interface. In an embodiment, the intravascular device 102 includes a memory component (e.g., an electrically erasable programmable read-only memory or EEPROM, or other suitable device) disposed adjacent to or within the catheter hub 118 that stores data about the intravascular device 102. Electric signals to and/or from the computing device 130 that are associated with accessing data from the memory component can be transmitted via the slip ring assembly.

The interface module 120 also facilitates communication of signals between the computing device 130 and the intravascular device 102 to control the operation of the transducer subassembly 108. Controlling the operation of the transducer subassembly 108 can include generating control signals to configure the transducer element, generating excitation signals to trigger the transducer element to emit ultrasonic energy, and/or forwarding echo signals captured by the transducer element to the computing device 130. With regard to the echo signals, the interface module 120 forwards the received signals to the computing device 130 and, in some embodiments, performs preliminary signal processing prior to transmitting the signals to the computing device 130. In examples of such embodiments, the interface module 120 performs amplification, filtering, and/or aggregating of the data. In that regard, the interface module 120 can include a printed circuit board with one or more electronic components to perform the functions described herein. In an embodiment, the interface module 120 also supplies high- and low-voltage DC power to support operation of the circuitry within the transducer subassembly 108. For example, DC signal can be transmitted to an amplifier of the transducer subassembly 108. Time-varying radiofrequency (RF) signals from the transducer subassembly 108 can be transmitted to the computing device 130. The signals described herein and other signals can be transmitted between the computing device 130 and the intravascular device 102 via the slip ring assembly of the interface module 120. The intravascular device 102 includes conductor(s) within the transducer shaft 106 to facilitate transmission of electric signals between the transducer subassembly 108 and the catheter hub 118. In that regard, one, two, three, four, five, six, seven, or more conductors can be disposed within the transducer shaft 106. Similarly, the interface module 120 includes one, two, three, four, five, six, seven, or more conductors to facilitate the transmission of electric signals between a connector and a spinning element of the slip ring assembly. A four-wire arrangement is described in U.S. patent application Ser. No. 13/892,045, filed May 10, 2013, the entirety of which is hereby incorporated by reference herein.

The computing device 130 receives the data from the transducer subassembly 108 by way of the interface module 120 and processes the data to create an image of the tissue surrounding the transducer assembly 108. The computing device 130 may also display the image on the display device 140.

Figure 2:
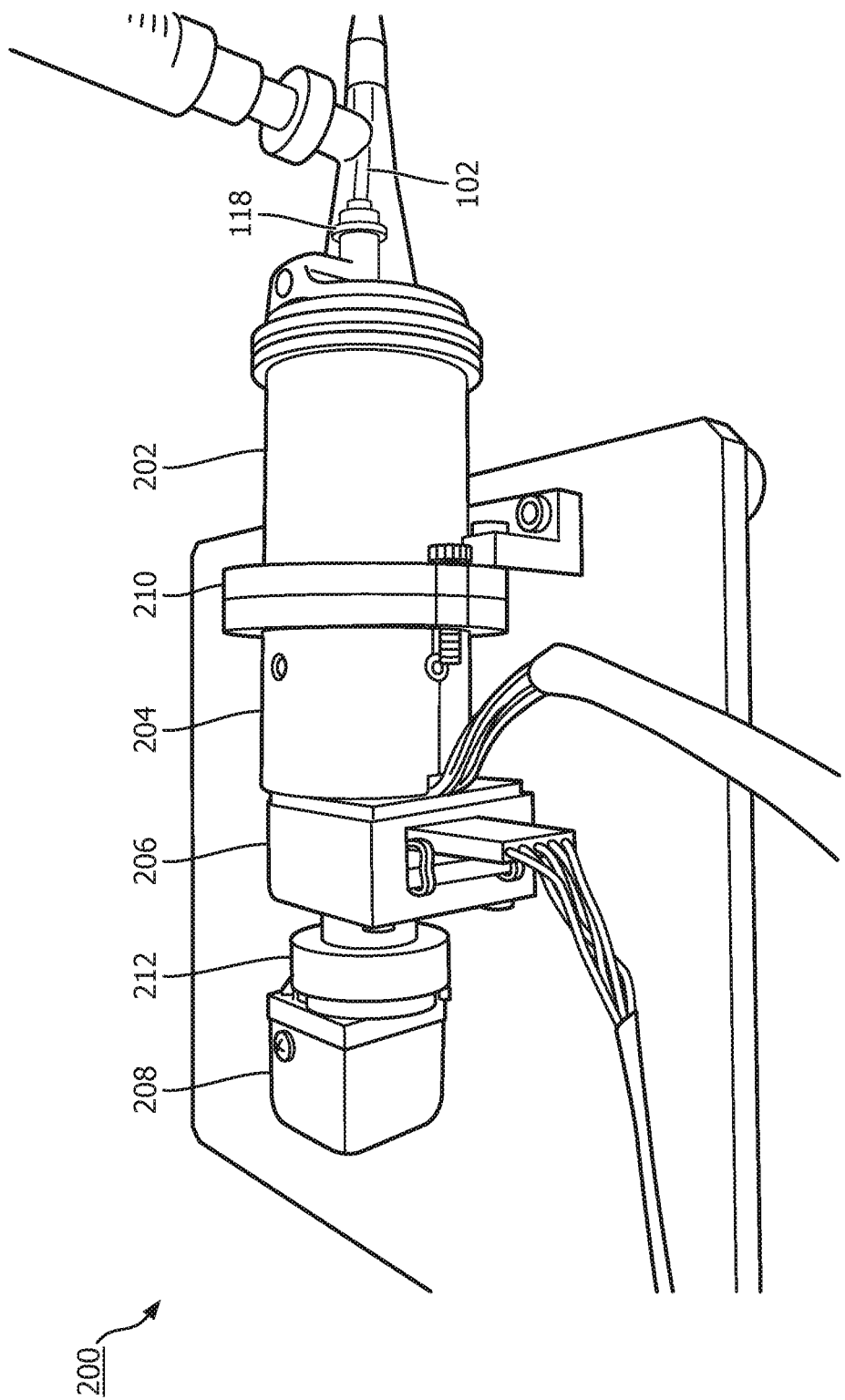
FIG. 2 is a perspective view of an interface module according to aspects of the present disclosure.

FIGS. 2, 3a, and 3b illustrate an interface module according to an embodiment of the present disclosure. FIG. 2 is a perspective view of the interface module 200, FIG. 3a is a diagrammatic side view of the interface module 200, and FIG. 3b is a diagrammatic, cross-sectional, top view of the interface module 200 taken along section line 3b-3b of FIG. 3a. The interface module 200 is similar to the interface module 120 of FIG. 1. FIG. 2 is similar to FIGS. 3a and 3b except that their orientations differ by 180°. That is, the proximal side of the interface module 200 is on the left side of FIG. 2, while the proximal side of the interface module 200 is on the right side of FIGS. 3a and 3b. At a high level, the interface module 200 includes a connector 202, motor 204, and slip ring assembly 208.

The connector 202 provides mechanical and electrical connection between interface module 200 and the intravascular device 102. The connector 202 includes a mating component 320 that mechanically receives or is received within a corresponding mating component of the catheter hub 118 (FIG. 1). The connector 202 is rotatably coupled to the proximal end of the transducer shaft 106 (FIG. 1) via the mating component 320. For example, the mating component 320 is capable of rotating such that rotation caused by the motor 204 can be transmitted to the drive cable 122 (FIG. 1). The mating component 320 includes electrical contacts such that the intravascular device 102 (e.g., the transducer subassembly 108) and the interface module 120 are electrically connected. In the illustrated embodiments, the mating component 320 includes four contacts.

The motor 204 controls rotation of the drive cable 122 and the transducer subassembly 108 (FIG. 1) of the intravascular device 102. The motor 204 also controls rotation of a spinning element 310 of a slip ring assembly 208. In that regard, the motor 204 is mechanically connected (directly or indirectly) to the mating component 320 of the connector 202 and spinning element 310. For example, the motor 204 includes rotating shaft 330 that is coupled to the mating component 320 and the spinning element 310. In the embodiment of FIGS. 2, 3a, and 3b, the motor 204 is disposed between the connector 202 and the spinning element 310 of the slip ring assembly 208. In an embodiment, the motor 204 drives the shaft 330 to rotate at 1800 revolutions per minute, which corresponds to IVUS images generated by the computing device 130 and displayed by the display device 140 (FIG. 1) at 30 frames per second. In various embodiments, the motor can be driven at different rotational frequencies.

The motor 204 can be fabricated and/or otherwise acquired with the shaft 330 extending therethrough. For example, the shaft 330 can be concentrically disposed within the motor 204 and extend longitudinally through the motor. The shaft 330 can at least partially extend through one or more components of the interface module 200 (e.g., the connector 202, the motor 204, the encoder 206, and/or the slip ring assembly 208). The shaft 330 does not extend completely through the slip ring assembly 208 in some embodiments. The shaft 330 can completely extend through one or more components of the interface module 220 (e.g., the motor 204 and/or the encoder 206). Thus, the motor 204 and/or the encoder 206 can be positioned in any configuration between the connector 202 and the slip ring assembly 208. The shaft 330 can be a unitary component or can be composed of two or more constituent parts.

In some embodiments, the shaft 330 is hollow. That is, an interior of the shaft 330 can include a lumen to allow passage of one or more conductors from the connector 202 to the slip ring assembly 208. In that regard, a plurality of conductors are disposed at least partially within the shaft 330 to electrically couple the mating component 320 with the spinning element 310 of the slip ring assembly 208. In an embodiment, four conductors are disposed within the shaft 330 and extend between the connector 202 and the slip ring assembly 208. For example, when the transducer subassembly 108 (FIG. 1) includes a PMUT, one or more of the four conductors can transmit AC excitation signals to the transducer subassembly 108, DC power to an amplifier electrically connected to the PMUT, and/or AC return signals from the transducer subassembly 108 to the computing device 130. In other embodiments, more or fewer conductors are provided within the interface module 200. For example, one, two, three, four, five, six, seven, or more conductors can be provided within the interface module 200. In some embodiments, in addition to the four conductors related to transducer operation described above, a fifth conductor can be provided to facilitate communication of signals between the computing device 130 and a memory component (e.g., EEPROM) of the intravascular device 102. In some embodiments, a sixth conductor can be provided to electrically couple the shaft 330 to ground. In some embodiments, not all of the conductors disposed within the shaft 330 extend between the connector 202 and the slip ring assembly 208. For example, the sixth conductor for grounding the shaft 330 can be provided within the interface module 200 at or near the proximal portion of the shaft 330.

Slip ring assembly 208 is a mechanical device comprised of electrically conductive rings and brushes. The slip ring assembly 208 also provides a transition between rotating and stationary portions of the interface module 120 and the IVUS imaging system 100 more generally. The slip ring assembly 208 includes a spinning element 310. The spinning element 310 can include one or more conductive rings mounted on a slip ring shaft or cylinder that rotates when driven by the motor 204. In other embodiments, the conductive rings are stationary, while the motor 204 drives rotation of the brushes. It is understood that the conductive rings can be made of any suitable conductive material, including gold, silver, other precious metals, etc. The plurality of conductive rings of the slip ring shaft 310 can be electrically isolated from one another. The number of conductive rings on the slip ring shaft 310 varies and can be as many as required to facilitate transfer of the DC and AC signals related to operation of the intravascular device 102. In an embodiment, the slip ring shaft 310 includes the same number of conductive rings as there are conductors within the interface module 102. For example, the slip ring shaft 310 can include one, two, three, fourth, five, six, seven, or more conductive rings. Each of the conductors within the interface module 102 can terminate at one of the conductive rings and be electrically and/or mechanically coupled thereto.

The slip ring assembly 208 includes a stationary element 312. The stationary element 312 can include one or more brushes, springs, and/or other suitable contact elements. The stationary element 312 is disposed proximate the spinning element 310 such that the brushes of the stationary element 312 and the conductive rings of spinning element 310 are in mechanical contact. As a result, the stationary element 312 and the intravascular device 102 are electrically connected via the slip ring assembly 208. The stationary element can be made of any suitable conductive material including, e.g., gold, silver, other precious metals, etc. The stationary element is non-rotating. In that regard, the slip ring assembly includes a pin 340 that prevents rotation of the stationary element 312 while the spinning element 310 rotates. When the motor shaft 330 and slip ring shaft rotate 310, the wiping action of the brushes on the conductive rings provides an electrical connection. Because the conductive rings and brushes provide direct electrical connection across the rotating interface, both time varying and DC signals can be passed from the stationary to the rotating side. Each of a plurality of conductors 342 is electrically connected to a corresponding portion of the stationary element 312. The plurality of conductors 342 can transmit signals to and from the computing device 130 (FIG. 1). In some embodiments, a slip ring assembly available from Moog Inc. of East Aurora, N.Y. is implemented in the interface module 200 as the slip ring assembly 208.

In some embodiments, the interface module 200 includes an encoder 206. Encoder 206 is utilized to provide motion control for the motor 204. In particular, encoder 206 ensures that the motor 204 is accurately and precisely driven at the desired frequency (e.g., 1800 RPM). The encoder 206 can provide comparatively higher resolution control over rotational frequency, which in turn leads to more stable rotational frequency during operation and ultimately better IVUS image quality. The encoder 206 also generates positional information for the motor 204 to provide accurate ultrasound signal synchronization. For example, encoder 206 can track a rotation of the motor 204 such that computing device 130 is triggered to start a new IVUS image frame at each revolution (e.g., one frame per revolution). The encoder 206 also tracks the rotation of the motor 204 to control the transducer firing sequence. For example, the transducer subassembly 108 is triggered to fire a desire number of times and at desired intervals during each revolution (e.g., 512 firings per revolution at equally spaced intervals). In the embodiment of FIGS. 2a, 3a, and 3b, the encoder 206 is disposed between the motor 204 and the slip ring assembly 208. The shaft 330 and the plurality of conductors disposed therein can extend through the encoder 206.

In some embodiments, the interface module 200 includes spacing elements 210 and 212 that ensure appropriate spacing and facilitate mechanical connection between the connector 202, the motor 204, the encoder 206, and/or the slip ring assembly 208. In the embodiment of FIGS. 2a, 3a, and 3b, the spacing element 210 is disposed between the connector 202 and the motor 204, while the spacing element 212 is disposed between the encoder 206 and the slip ring assembly 208. The shaft 330 and the plurality of conductors disposed therein can extend through one or both of the spacing elements 210, 212.

Figure 4A:
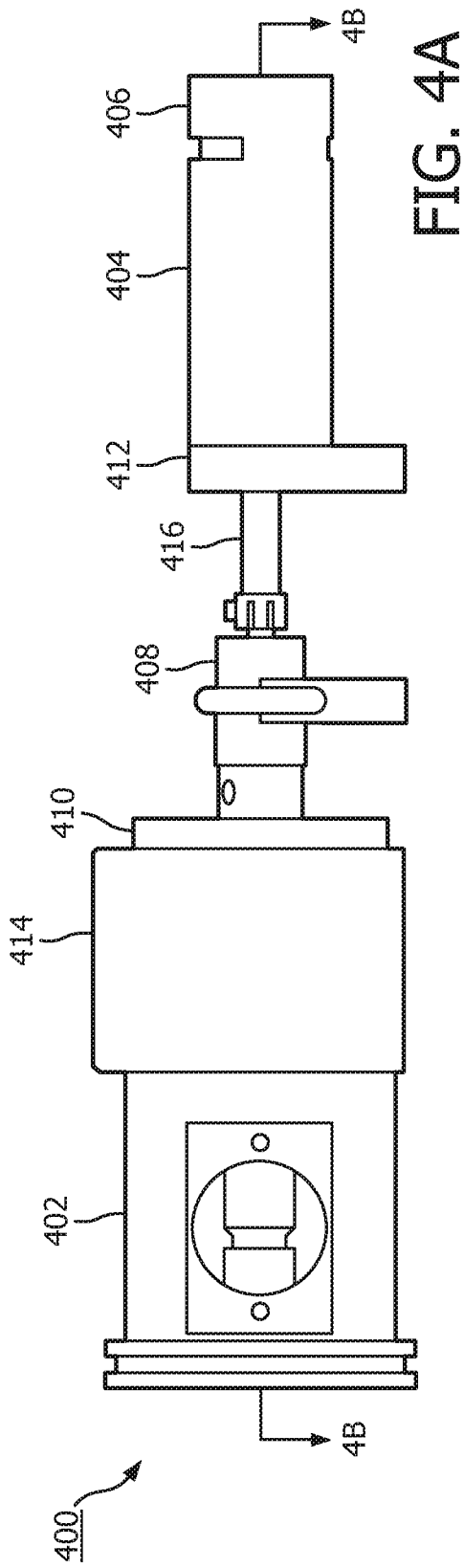
FIG. 4a is a diagrammatic side view of an interface module according to aspects of the present disclosure.
Figure 4B:
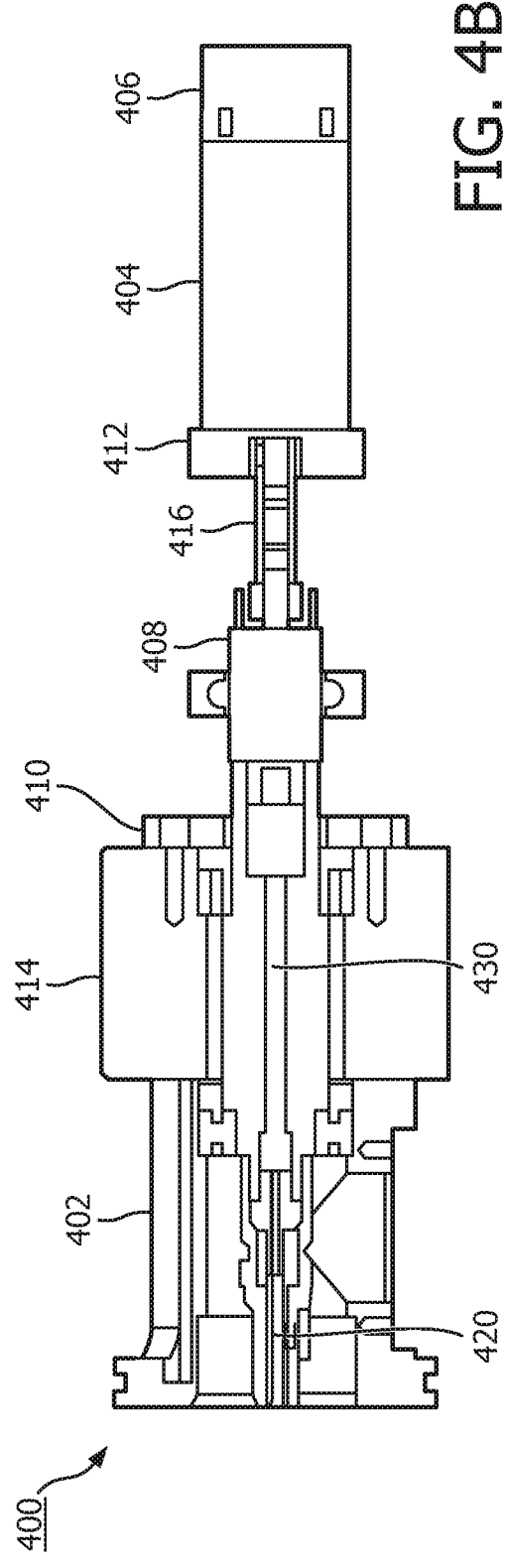

FIGS. 4a and 4b illustrate an interface module according to another embodiment of the present disclosure. FIG. 4a is a diagrammatic side view of the interface module 200, and FIG. 4b is a diagrammatic, cross-sectional, top view of the interface module 200 along section line 4b-4b of FIG. 4a.

The interface module 400 is similar to the interface module 120 of FIG. 1 and the interface module 200 of FIGS. 2, 3a, and 3b. However, a slip ring assembly 408 of the interface module 400 is configured such that a rotatable, hollow shaft 430 extends entirely through the slip ring assembly 408. The shaft 430 is coupled to and extends between a connector 402 and a motor 404. Because the shaft 430 extends entirely through the slip ring assembly 408, the slip ring assembly 408 can be placed anywhere in the interface module 400 between the connector 402 and the motor 404. For example, the slip ring assembly 408 can be positioned to maximize the distance from the motor 404 such that relatively less noise affects the slip ring assembly 408.

The connector 402, the motor 404, and the slip ring assembly 408 are respectively similar to the connector 202, the motor 204, and the slip ring assembly 208 (FIGS. 2, 3a, and 3b). In that regard, connector 402 is rotatably coupled to a proximal end of the transducer shaft 106 (FIG. 1) via the mating component 420. The mating component 420 mechanically and electrically couples the intravascular device 102 and the interface module 400 when connected to the catheter hub 118 (FIG. 1). The mating component 420 is similar to mating component 320 (FIGS. 2, 3a, and 3b). The shaft 430 can be hollow such that the shaft 430 includes a lumen to allow passage of one or more conductors from the connector 402 to the slip ring assembly 408. For example, the one or more conductors can extend between the mating component 420 and the slip ring assembly 408. The shaft 430 is similar to the shaft 330 (FIGS. 2, 3a, and 3b). In some embodiments, the shaft 430 is a unitary component, while in other embodiments, the shaft 430 is composed of two or more constituent portions. In the embodiment of FIGS. 4a and 4b, the slip ring assembly 408 is disposed between the connector 402 and the motor 404. Accordingly, the shaft 430 extends through the slip ring assembly 408, between the mating component 420 and the motor 404. The shaft 430 does not extend completely through the motor 404 and/or the encoder 406 in some embodiments. In some embodiments, a slip ring assembly available from Electro-Miniatures Corp. of Moonachie, N.J. is implemented in the interface module 400 as the slip ring assembly 408. The interface module 400 also includes an encoder 406 that is similar to the encoder 206 (FIGS. 2, 3a, and 3b). In some embodiments, the encoder 406 is integrally formed with the motor 404. In other embodiments, the encoder 406 and the motor 404 are separate components. In the embodiment of FIGS. 4a and 4b, the motor 404 is disposed between the slip ring assembly 408 and the encoder 406. The interface module 400 also includes spacer elements 410, 412, 414, and 416 to ensure appropriate spacing and facilitate mechanical connection between connector 402, slip ring assembly 408, and motor 404. The spacer elements 410 and 414 are disposed between connector 402 and the slip ring assembly 408. The spacer elements 412 and 416 are disposed between the slip ring assembly 408 and the motor 404. The shaft 430 extends through the spacer elements 410, 412, 414, and 416. The spacer elements 410, 412, 414, and 416 can be similar to the spacer elements 210, 212 (FIGS. 2, 3a, and 3b).

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. For example, the features of various embodiments can be combined with features of different embodiments. One or more steps can be added to or removed from the methods described herein. A person of ordinary skill in the art will understand that the steps of the method can be performed in an order different than the order described herein. It is understood that such variations may be made to the foregoing without departing from the scope of the present disclosure. Accordingly, it is appropriate that the appended claims be construed broadly and in a manner consistent with the present disclosure.

What is claimed is:

1. An intravascular ultrasound (IVUS) imaging system, comprising:
    an intravascular device including:
        a transducer shaft comprising a distal end;
        an ultrasound transducer positioned at the distal end and configured to provide AC return signals representative of ultrasound data; and
        an electronic component in communication with the ultrasound transducer and positioned at the distal end, the electronic component configured to receive DC signals; and
    an interface module removably coupled to the intravascular device, the interface module including:
        a connector rotatably coupled to a proximal end of the transducer shaft;
        a motor coupled to the connector;
        a spinning element coupled to the motor, wherein the spinning element comprises four conductive rings;
        a stationary element comprising a plurality of brushes, wherein the stationary element is disposed proximate the spinning element such that a different one of the plurality of brushes is in mechanical contact with each of the four conductive rings; and
        four conductors coupled to the connector and the spinning element such that the stationary element and the intravascular device are in electrical communication,
        wherein the stationary element is configured to receive the AC return signals from the ultrasound transducer via at least a first conductor of the four conductors, and to transmit the DC signals supplied by the interface module to the electronic component via at least a second conductor of the four conductors, and
        wherein the interface module is configured to perform signal processing on the AC return signals and output the processed AC return signals.

2. The IVUS imaging system of claim 1, wherein the electronic component is in electrical communication with the stationary element of the interface module.

3. The IVUS imaging system of claim 2, wherein the ultrasound transducer comprises a piezoelectric micromachined ultrasonic transducer (PMUT).

4. The IVUS imaging system of claim 3, wherein the electronic component comprises an amplifier.

5. The IVUS imaging system of claim 1, wherein the intravascular device further comprises four conductors coupled to the ultrasound transducer and a connector hub at the proximal end of the transducer shaft, wherein, when the connector hub of the intravascular device is connected to the connector of the interface module, the stationary element of the interface module is in electrical communication with the ultrasound transducer.

6. The IVUS imaging system of claim 1, wherein the motor is disposed between the connector and the spinning element.

7. The IVUS imaging system of claim 6, wherein the interface module further comprises a hollow shaft extending through the motor, and between the connector and the spinning element.

8. The IVUS imaging system of claim 7, wherein the four conductors are at least partially disposed within the hollow shaft.

9. The IVUS imaging system of claim 8, wherein the hollow shaft is electrically grounded.

10. The IVUS imaging system of claim 8, wherein the interface module comprises at least five conductors.

11. The IVUS imaging system of claim 6, wherein the spinning element is disposed proximal to the motor and the connector.

12. The IVUS imaging system of claim 1, further comprising a computing device in electrical communication with the interface module,
wherein the AC signals provided by the ultrasound transducer comprise ultrasound data obtained by the ultrasound transducer, and
wherein the interface module is configured to perform signal processing on the AC signals and transmit the AC signals from the at least the first conductor to the computing device.

13. An interface module for an intravascular ultrasound imaging system, the interface module comprising:
a connector rotatably coupled to a transducer shaft of an intravascular device, the intravascular device comprising an ultrasound transducer and a first electronic component positioned at a distal end of the transducer shaft;
a motor coupled to the connector;
a spinning element coupled to the motor, wherein the spinning element comprises four conductive rings;
a stationary element comprising a plurality of brushes, wherein the stationary element is disposed proximate the spinning element such that a different one of the plurality of brushes is in mechanical contact with each of the four conductive rings;
a second electronic component in electrical communication with the intravascular device and coupled to the stationary element; and
four conductors coupled to the connector and the spinning element such that the stationary element and the intravascular device are in electrical communication,
wherein the stationary element is configured to receive AC return signals representative of ultrasound data from the ultrasound transducer via at least a first conductor of the four conductors, and to transmit DC signals supplied by the interface module to the first electronic component via at least a second conductor of the four conductors, and
wherein the second electronic component is configured to perform signal processing on the received AC return signals and output the processed AC return signals.

14. The interface module of claim 13, wherein the motor is disposed between the connector and the spinning element.

15. The interface module of claim 14, further comprising a hollow shaft extending through the motor, and between the connector and the spinning element, wherein the four conductors are at least partially disposed within the hollow shaft.

16. The interface module of claim 15, wherein the hollow shaft is electrically grounded.

17. The interface module of claim 14, wherein the spinning element is disposed proximal to the motor and the connector.

18. An interface module for an intravascular ultrasound device, the interface module comprising:
a connector rotatably coupled to a transducer shaft of the intravascular ultrasound device, the intravascular ultrasound device comprising an ultrasound transducer and a first electronic component positioned at a distal end of the transducer shaft;
a motor coupled to the connector such that the connector rotates when the motor is activated, wherein the motor comprises a hollow shaft extending therethrough;
a slip ring assembly coupled to the motor, wherein the slip ring assembly includes a plurality of conductive rings and a plurality of brushes, wherein each of the plurality of brushes are in mechanical contact with at least one of the plurality of conductive rings, and wherein the slip ring assembly is coupled to the motor such that the plurality of conductive rings rotates when the motor is activated;
a second electronic component in electrical communication with the intravascular ultrasound device; and
a plurality of conductors at least partially disposed within the hollow shaft, wherein the plurality of conductors electrically couple the connector and the plurality of conductive rings,
wherein the slip ring assembly is configured to receive AC return signals representative of ultrasound data from the ultrasound transducer via at least a first conductor of the plurality of conductors, and to transmit DC signals supplied by the interface module to the first electronic component via at least a second conductor of the plurality of conductors,
wherein the second electronic component is configured to perform signal processing on the received AC return signals and output the processed AC return signals.

19. The interface module of claim 18, wherein the plurality of conductors comprises at least four conductors.

20. The interface module of claim 18, wherein the hollow shaft is electrically grounded.

21. The interface module of claim 18, wherein the motor is disposed between the connector and the slip ring assembly.

22. The interface module of claim 21, wherein the slip ring assembly is disposed proximal to the motor and the connector.

* * * * *